(12) United States Patent
Haldenby et al.

(10) Patent No.: US 10,284,378 B2
(45) Date of Patent: May 7, 2019

(54) CERTIFICATE AUTHORITY MASTER KEY TRACKING ON DISTRIBUTED LEDGER

(71) Applicant: The Toronto-Dominion Bank, Toronto (CA)

(72) Inventors: Perry Aaron Jones Haldenby, Toronto (CA); Arthur Carroll Chow, Toronto (CA); Paul Mon-Wah Chan, Toronto (CA); John Jong Suk Lee, Toronto (CA); Linda Tao, Toronto (CA)

(73) Assignee: The Toronto-Dominion Bank, Toronto (CA)

( * ) Notice: Subject to any disclaimer, the term of this patent is extended or adjusted under 35 U.S.C. 154(b) by 156 days.

(21) Appl. No.: 15/285,757

(22) Filed: Oct. 5, 2016

(65) Prior Publication Data

US 2018/0097638 A1 Apr. 5, 2018

(51) Int. Cl.
| | |
|---|---|
| *H04L 9/32* | (2006.01) |
| *H04L 9/30* | (2006.01) |
| *H04L 29/06* | (2006.01) |
| *H04L 9/08* | (2006.01) |
| *H04L 9/14* | (2006.01) |
| *H04W 12/04* | (2009.01) |
| *H04W 12/06* | (2009.01) |

(52) U.S. Cl.
CPC .......... *H04L 9/3263* (2013.01); *H04L 9/0861* (2013.01); *H04L 9/14* (2013.01); *H04L 9/302* (2013.01); *H04L 9/3247* (2013.01); *H04L 9/3249* (2013.01); *H04L 63/0442* (2013.01); *H04L 63/06* (2013.01); *H04L 63/0823* (2013.01); *H04W 12/04* (2013.01); *H04W 12/06* (2013.01)

(58) Field of Classification Search
CPC ......... H04L 63/06; H04L 9/14; H04L 9/3249; H04L 9/302; H04L 9/3263; H04L 9/0861; H04L 9/3247; H04W 12/04
See application file for complete search history.

(56) References Cited

U.S. PATENT DOCUMENTS

| | | | |
|---|---|---|---|
| 6,195,433 B1 * | 2/2001 | Vanstone | H04L 9/3066 380/285 |
| 2013/0007442 A1 * | 1/2013 | Mao | H04L 63/0823 713/156 |
| 2016/0254910 A1 * | 9/2016 | Finlow-Bates | H04L 9/0891 713/158 |

OTHER PUBLICATIONS

Salowey et al. "Specification for the Derivation of Root Keys from an Extended Master Session Key (EMSK)", Aug. 2008, pp. 1-20.*

(Continued)

*Primary Examiner* — Alexander Lagor
*Assistant Examiner* — Wu V Tran
(74) *Attorney, Agent, or Firm* — Duane Morris LLP

(57) ABSTRACT

An apparatus for use in a digital messaging system includes a storage device and a processor coupled to the storage device. The storage device storing software instructions for controlling the processor that when executed by the processor configured the processor to: generate a master private and public key pair; associate the master private and public key pair with a first certificate; and derive at least one domain-specific key from the one of the master private and public key pair. The first certificate is registered to a group comprising a plurality of domains. The domain-specific key is associated with one of the plurality of domains.

9 Claims, 7 Drawing Sheets

(56) References Cited

OTHER PUBLICATIONS

N. Fotiou and G. C. Polyzos, "Decentralized name-based security for content distribution using blockchains," 2016 IEEE Conference on Computer Communications Workshops (INFOCOM WKSHPS), San Francisco, CA, 2016, pp. 415-420 (Year: 2016).*

J. Salowey, Specification for the Derivation of Root Keys from an Extended Master Session Key (EMSK) (Year: 2008).*

* cited by examiner

CERTIFICATE AUTHORITY MASTER KEY TRACKING ON DISTRIBUTED LEDGER

BACKGROUND

Communication of sensitive information through multiple parties presents issues of data interception, unauthorized viewing, and/or data control and validation. For example, middle parties (such as brokers) may read and/or modify the data during transmission. End-to-end encryption has been used to mask data traveling through transmission channels. However, end-to-end encryption is restrictive and prevents certain use cases which require an intermediate party to pre-process and/or read restricted portions of the data.

Current certificate systems rely on trusted third parties to issue and maintain authentication certificates. Such certificates are vulnerable to theft. In addition, if a false certificate authority is established and/or a legitimate certificate authority is compromised, fake certificates can be generated for one or more known domains and used to sign false messages or other communications.

SUMMARY

In various embodiments, an apparatus for use in a digital messaging system is disclosed. The apparatus includes a storage device and a processor coupled to the storage device. The storage device storing software instructions for controlling the processor that when executed by the processor configured the processor to: generate a master private and public key pair; associate the master private and public key pair with a certificate; and derive at least one domain-specific key from the one of the master private and public key pair. The certificate is registered to a group comprising a plurality of domains. The domain-specific key is associated with one of the plurality of domains.

In various embodiments, an apparatus for use in a digital messaging system is disclosed. The apparatus includes a storage device and a processor coupled to the storage device. The storage device storing software instructions for controlling the processor that when executed by the processor configured the processor to: generate a master key generation request; transmit the master key generation request to a certificate authority implemented on a distributed ledger; and receive a derived domain-specific key. The certificate authority is configured to generate a master public and private key pair and a certificate. The certificate is stored on the distributed ledger. The domain-specific key is derived from the master public and private key pair.

In various embodiments, a method of certificate validation is disclosed. The method includes generating a certificate generation request. The certificate generation request includes a plurality of domains associated with a group. The certificate generation request is transmitted to a certificate authority. The certificate authority includes one or more programs configured to execute on a distributed ledger. At least one derived domain-specific key is received from the certificate authority. The derived domain-specific key is derived from a master group key generated by the certificate authority.

BRIEF DESCRIPTION OF THE FIGURES

The following will be apparent from elements of the figures, which are provided for illustrative purposes and are not necessarily to scale.

DETAILED DESCRIPTION

This description of the exemplary embodiments is intended to be read in connection with the accompanying drawings, which are to be considered part of the entire written description. The use of the singular includes the plural unless specifically stated otherwise. The use of "or" means "and/or" unless stated otherwise. Furthermore, the use of the term "including," as well as other forms such as "includes" and "included," is not limiting. In addition, terms such as "element" or "component" encompass both elements and components comprising one unit, and elements and components that comprise more than one subunit, unless specifically stated otherwise. Additionally, the section headings used herein are for organizational purposes only, and are not to be construed as limiting the subject matter described.

Figure 1:
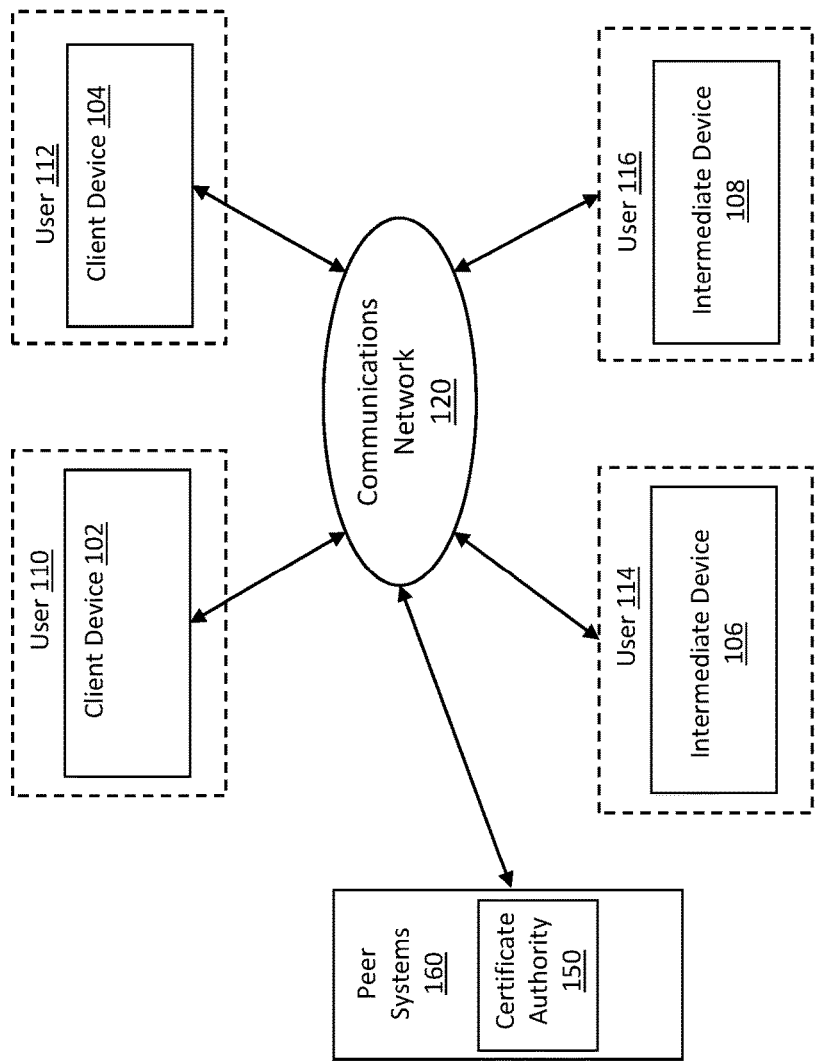
FIG. 1 is a block diagram of a system, in accordance with some embodiments.

FIG. 1 is a block diagram of a system 100 in accordance with some embodiments of the present disclosure. System 100 may be a computing environment including client devices 102, 104, intermediate devices 106, 108, one or more peer systems 160, and a communications network 120 connecting various components of system 100. Although two client devices 102, 104 and two intermediate devices 106, 108 are shown in this example, any number of client devices and/or intermediate devices may be present. Various components of computing environment 100 are configured to address problems associated with conventional end-to-end encrypted communication and certificate authorities by providing a system and method configured for secure, path agnostic transmission of one or more messages. In some embodiments, the disclosed systems and method eliminate the need for trusted intermediate systems.

Figure 2:
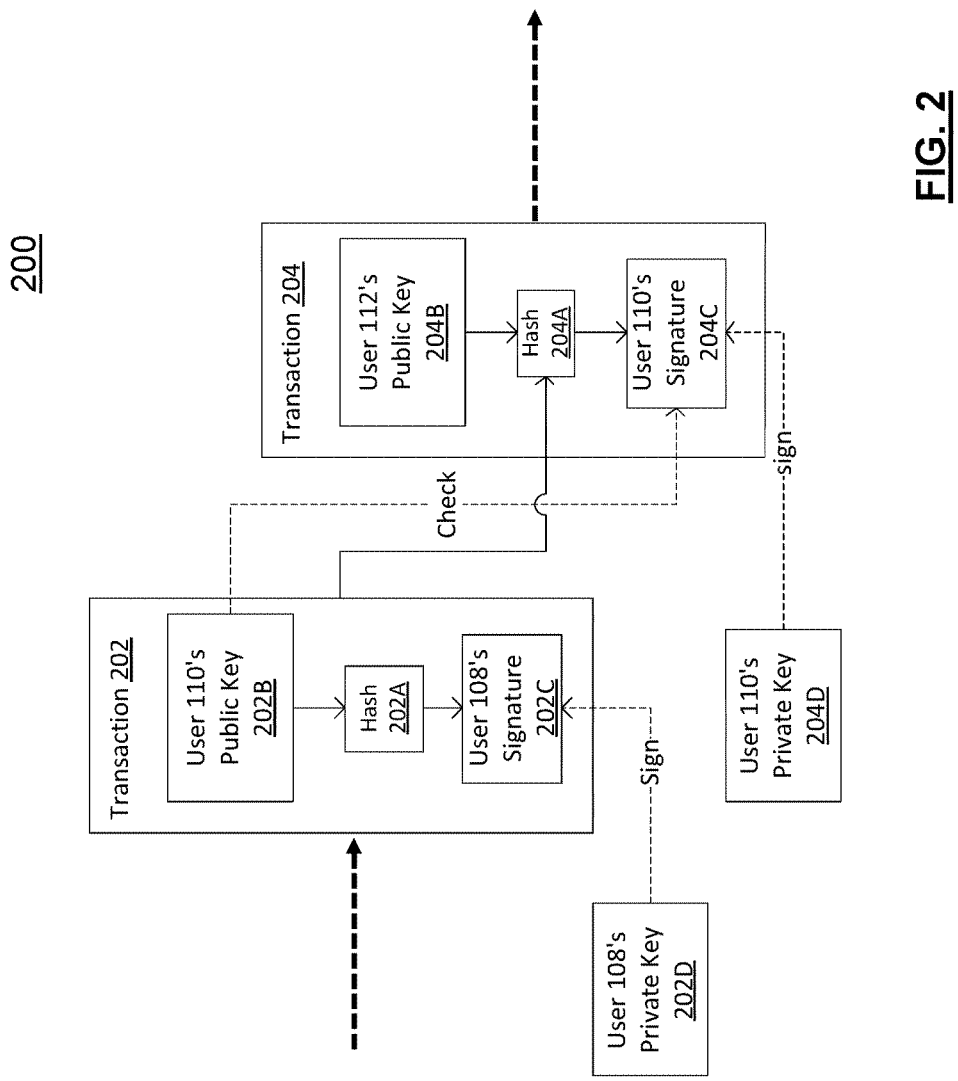
FIG. 2 is a block diagram of a conventional distributed ledger, in accordance with some embodiments.

FIG. 2 is a diagram of a structure 200 of a distributed ledger, which may be generated through the interaction of components of computing environment 100. In the example of FIG. 2, user 110 is associated with client device 102, which executes a stored software application (e.g., an access application) capable of obtaining a current version of a distributed ledger from one or more networked computer systems (e.g., one of peer systems 160 configured to "mine" broadcasted transaction data and update ledgers). In some embodiments, a distributed ledger may represent a "longest" distributed ledger than includes a maximum number of discrete "blocks." The blocks identify respective transactions performed by the distributed ledger 200, such as one or more certificate authority transactions.

FIG. 2 shows blocks corresponding to two transactions 202 and 204, with arrows to the left and right of these transactions indicating that these are merely two transactions in a potentially longer series of chained blocks (hence the term "block-chain ledger"). In the first transaction (transaction 202) depicted in FIG. 2, user 110 registers a public/private key pair and a digital certificate with a certificate authority (CA) stored on the distributed ledger 200. In the second transaction (transaction 204), the CA generates one or more requested child keys as discussed in more detail below.

One or more of peer systems 160 may receive the data specifying transactions 202, 204 from client device 104. In certain instances, peer systems 160 may act as "miners" for the distributed ledger, and may competitively process the received transaction data (either alone or in conjunction with other data) to generate additional blocks of the ledger, which may be appended to the distributed ledger and distributed across peer systems 160 (e.g., through a peer-to-peer network) and to other connected devices of environment 100.

Distributed ledger architectures enable the public (or a selected group of brokers and/or systems) to review content of the ledgers and verify ownership details. The decentralized nature of distributed ledgers enable multiple distributed networks to verify the contents of a single ledger. The resulting redundancy may render distributed ledger architecture more robust than centralized server systems, and effectively eliminates the falsification of ledger data by malicious parties.

Client Devices

Referring back to FIG. 1, each of the client devices 102, 104 and/or the intermediate devices 106, 108 may include a computing device, such as a hashing computer, a personal computer, a laptop computer, a tablet computer, a notebook computer, a hand-held computer, a personal digital assistant, a portable navigation device, a mobile phone, a smart phone, a wearable computing device (e.g., a smart watch, a wearable activity monitor, wearable smart jewelry, and glasses and other optical devices that include optical head-mounted displays (OHMDs), an embedded computing device (e.g., in communication with a smart textile or electronic fabric), and/or any other type of computing device that may be configured to store data and software instructions, execute software instructions to perform operations, and/or display information on a display device. At least one of client devices 102, 104 may be associated with one or more users, such as users 110, 112, as shown in FIG. 1. In some embodiments, each of the client devices 102, 104 and/or the intermediate devices 106, 108 can be associated with one or more members of a group, such as, for example, one or more brokers Each client device 102, 104 and/or intermediate device 106, 108 includes one or more tangible, non-transitory memories that store data and/or software instructions, and one or more processors configured to execute software instructions. Client devices 102, 104 and/or intermediate devices 106, 108 may include one or more display devices that display information to a user and one or more input devices (e.g., keypad, keyboard, touchscreen, voice activated control technologies, or any other type of known input device) to allow the user to input information to the client device.

In one aspect, each client device 102, 104 and/or intermediate device 106, 108 stores in memory one or more software applications that run on the device and are executed by the one or more processors. In some instances, each device stores software applications that, when executed by one or more processors, perform operations that establish communications with a certificate authority 150. The certificate authority 150 can comprise one or more programs (or smart contracts) implemented on the distributed ledger 200. The certificate authority 150 is configured to validate, maintain, revoke, and/or otherwise manage one or more certificates and/or private/public key pairs associated with one or more users 110, 112, devices 102-108, groups of devices, domains, and/or groups of domains.

Each client device 102, 104 may execute the stored software application(s) to generate a transaction that to request, updated, invalidate, and/or otherwise manage a certificate issued by the CA 150. The executed software applications may cause client devices 102, 104 to transmit the data specifying the transaction 202. In distributed ledger-based systems, the client devices 102, 104 transmit a transaction 202 to one or more peers 160 for processing.

Exemplary Intermediary Devices

Intermediary devices 106, 108 may be a computing systems configured to execute software instructions to perform one or more operations in accordance with various embodiments. In one aspect, each of the intermediary systems 106, 108 are associated with one or more brokers. The intermediary devices 106, 108 are configured to provide message validation and forwarding of one or more messages received over the network 120. For example, in some embodiments, each of the intermediary devices 106, 108 comprise a node in a distributed nodal network. A first client device 102 can transmit a message over the distributed nodal network. The message is forward by one or more intermediary devices 106, 108 to a second client device 104.

In one aspect, intermediate devices 106, 108 include computing components configured to store, maintain, and generate data and software instructions. For example, intermediate devices 106, 108 may include one or more servers (e.g., server 142) and tangible, non-transitory memory devices (e.g., data repository 144). Server 142 may include one or more computing devices configured to execute software instructions to perform one or more processes in accordance with various embodiments. In one example, server 142 is a computing device that executes software instructions to perform operations that provide information to at least one other component of computing environment 100. In one embodiment, server 142 includes a computer (e.g., a personal computer, network computer, or mainframe computer) having one or more processors that are selectively activated or reconfigured by a computer program Intermediate devices 106, 108 may be incorporated as corresponding nodes in a distributed network or as a corresponding networked server in a cloud-computing environment. Furthermore, server 142 may communicate via network 120 with one or more additional servers (not shown), which may facilitate the distribution of processes for parallel execution by the additional servers.

In further aspects, certificate authority 150 may represent a "controlling entity" capable of managing (e.g., issuing, maintaining, updating, revoking, etc.) various public and/or private key pairs and/or certificates stored on the distributed ledger 200, in accordance with various embodiments. For example, in some embodiments, the certificate authority 150 is a smart contract (e.g., computer code) uploaded to and executed by the distributed ledger 200 to replace the need for a trusted certificate authority under conventional certificate processes.

Exemplary Communications Networks

Communications network 120 may include one or more communication networks or media of digital data communication. Examples of communication network 120 include a local area network ("LAN"), a wireless LAN, a RF network, a Near Field Communication (NFC) network, (e.g., a "WiFi" network), a wireless Metropolitan Area Network (MAN) connecting multiple wireless LANs, NFC communication link(s), and a wide area network ("WAN"), e.g., the Internet. In accordance with various embodiments of the present disclosure, communications network 120 may include the Internet and any publicly accessible network or networks interconnected via one or more communication protocols, including, but not limited to, hypertext transfer protocol (HTTP) and transmission control protocol/internet protocol (TCP/IP). Communications protocols in accordance with various embodiments also include protocols facilitating data transfer using radio frequency identification (RFID) communications and/or NFC. Moreover, communications network 120 may also include one or more mobile device networks, such as a GSM network or a PCS network, allowing client device 102 to send and receive data via applicable communications protocols, including those described herein.

In some embodiments, the communications network 120 is a distributed nodal network including each of the client devices 102, 104 and/or the intermediate devices 106, 108 as nodes within the distributed nodal network.

Exemplary Certificate Authority on Distributed Ledger

In some embodiments, a distributed ledger 200 is configured to execute one or more programs uploaded and/or encoded therein. For example, in some embodiments, a distributed ledger 200 is configured to execute one or more programs (or smart contracts) in response to one or more transactions uploaded to the distributed ledger 200 and/or processed by the peers 160.

In some embodiments, a distributed ledger 200 can be configured as a CA 150 to generate, validate, maintain, revoke, and/or otherwise manage one or more certificates. The distributed ledger 200 can be a specific distributed ledger configured to operate as a CA 150 and/or can be a distributed ledger 200 configured to execute one or more programs uploaded to the distributed ledger 200, including a CA 150 contract (program) uploaded thereto.

In some embodiments, a distributed ledger 200 includes a trust-free CA 150 program configured to provide for registration of one or more certificates and/or one or more private/public key pairs. A client device 102 can generate a transaction request (such as transaction 202) that is uploaded to the distributed ledger 200 to register a public/private key pair. The client device 102 generates a transaction request which is provided to one or more peer systems 160 for processing. The transaction request includes one or more identifiers associated with the client device 102 and/or a user 110. For example, in some embodiments, the transaction request includes a public/private key pair generated by the client device 102, a key generating value for generating a public/private key pair, device-related information (such as Internet Protocol (IP) address, a uniform resource identifier (URI), a domain associated with the client device 102, a group of domains and/or client devices associated with a single master public/private key pair, and/or any other suitable identifier.

In some embodiments, the distributed ledger 200 generates a certificate that is associated with the public/private key pair and identifies the owners of the public/private key pair. For example, in some embodiments, the certificate identifies the client device 102 as an owner of the public/private key pair. As another example, in some embodiments, the certificate can identify a group of user devices 102, 104 and/or domains that share a single master private/public key pair. The private key and at least one public key allow the client device 104 and/or an associated user 108 to sign one or more communications and/or transactions. In some embodiments, the public/private keys are generated by a key generating running concurrently with the CA 150. The key generator can be located on the distributed ledger 200, locally on each of the client devices 102, 104, and/or on a remote system.

In some embodiments, one or more public keys issued to the client device 102 can be disseminated to additional client devices 112 for use in public-key encryption. For example, in some embodiments, a first public key issued for the client device 102 and paired with a private key is provide to at least a second client device 104. The second client device 104 can use the first public key to encrypt one or more messages intended for the first client device 102. A message encrypted with a first public key (or any public key associated with the first client device 102) can only be decrypted using the associated private key (i.e., asymmetric encryption).

In some embodiments, the CA 150 is configured to generate one or more child keys derived from a registered master public/private key pair. For example, in some embodiments, a client device 104 can transmit a transaction to one or more peers 160 to generate additional certificates having one or more public and/or private keys associated therewith. In some embodiments, each of the additionally generated public/private keys are derived from the master public/private key associated with the client device 102 and/or a group including the client device 102. In some embodiments, the master public/private key is a master public/private key associated with one or more client devices 102, 104. The CA 150 can generate child public/private keys derived from the master public/private keys and disseminate child keys to each of the client devices 102, 104 in the associated group. The CA 150 can generate the child public/private keys automatically upon registration of a master public/private key and/or can generate child public/private keys in response to a specific request from one or more client devices 102, 104.

In some embodiments, a client device 102 can generate a transaction to revoke one or more public and/or private keys or certificates on a distributed ledger 200. For example, in some embodiments, a client device 102 generates a transaction 204 which is provided to one or more peers 160. The transaction 202 updates the CA 150 to indicate that one or more public/private keys (such as a child public/private key pair) has been compromised and should be revoked. Revoked public and/or private keys are no longer valid and messages signed with the revoked public/private keys are ignored. By issuing only child public/private keys for use in active messaging and encryption, the CA 150 can protect the master public/private key of the group from exposure and reduce the overhead burden for reissuing compromised certificates.

Figure 3:
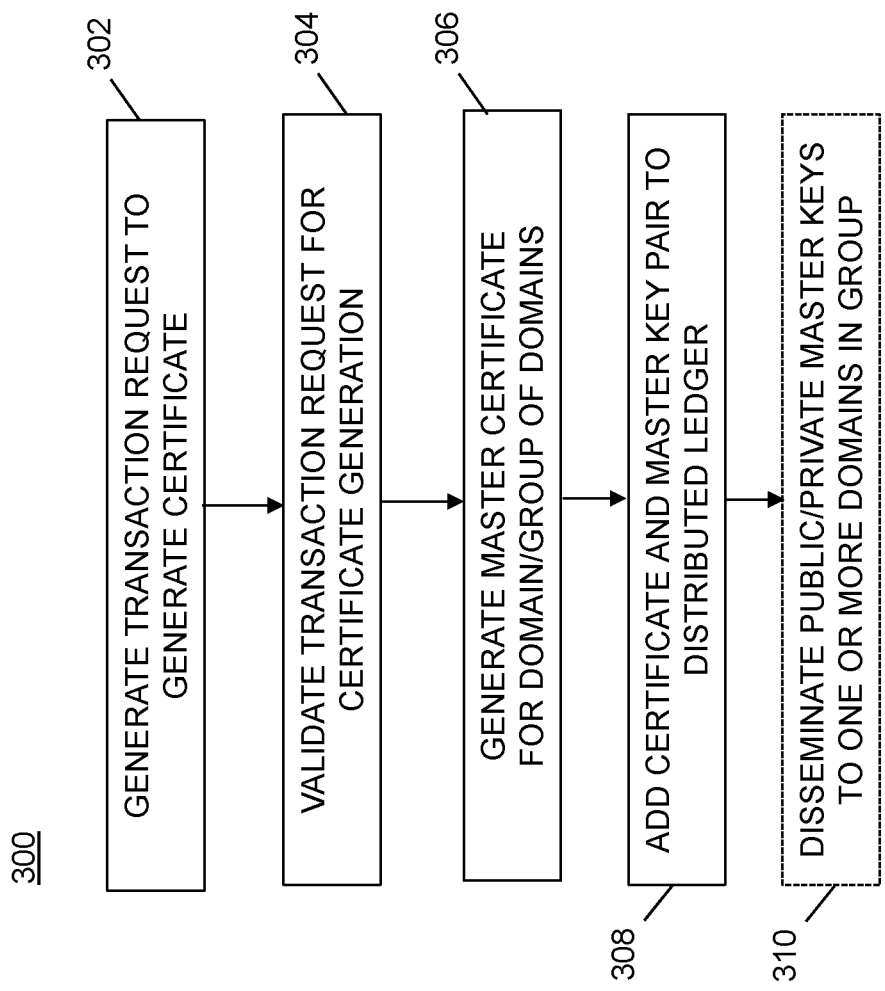
FIG. 3 is a flow chart of a method of registering a certificate with a certificate authority running on a distributed ledger, in accordance with some embodiments.

FIG. 3 illustrates a method 300 of registering and/or generating a certificate with a CA 150 stored on a distributed ledger 200. At step 302, a client device 102 generates a transaction request that is provided to one or more peers 160. The transaction request can include a request to generate a certificate for a specific domain (or set of domains) and a public/private key pair. The transaction request can further include one or more user identifiers to verify ownership of the included domain(s) and/or membership in an identified group. For example, in some embodiments, a token or other identifier is included in the transaction request to identify the client device 102 as a member of a closed group. The transaction request is provided to one or more peers 160.

At step 304, the one or more peers validate the transaction request. Validation of the transaction request can include verifying that the requested domain(s) and/or group is unregistered on the distributed ledger 200, verifying the user identifiers and ownership of the domain(s)/membership in a group, verifying the validity of the public/private key pairs, and/or any other suitable validation steps. In some embodiments, a predetermined number of peers 160 must validate the transaction request in order for the registration to be considered valid.

At step 306, a master certificate is generated for the domain/group. The master certificate identifies the domain/group as being associated with the uploaded public/private key pair. For example, in some embodiments, the first peer 160 to process the transaction request generates a certificate, one or more private/public key pairs, and/or any other suitable certificate element. The certificate can be generated according to one or more predetermined certificate generation processes, such as, for example, a Certificate Signing Request (CSR), a Secure Sockets Layer (SSL) process, and/or any other suitable signature process. The certificate elements can be provided to the client device 102 and/or can be maintained on the distributed ledger 200. In some embodiments, the certificate is hashed using one or more has functions and the hash of the certificate is stored on the distributed ledger. In some embodiments, the master certificate is used to generate one or more child certificates, as discussed in more detail below.

At step 308, the transaction request is validated and a transaction block 202 is added to the distributed ledger 200 registering the domain/group with certificate and the master public/private key pair. The transaction block 202 is distributed to multiple peers 160 each maintaining a local copy of the distributed ledger 200. In some embodiments, a predetermined number of peers 160 validate the registration upon receiving the transaction block 202.

At optional step 310, the master public/private keys are disseminated to one or more members of the domain/group, such as, for example, a client device 102, a client device 104, intermediate devices 106, 108, and/or any other suitable device.

Figure 4:
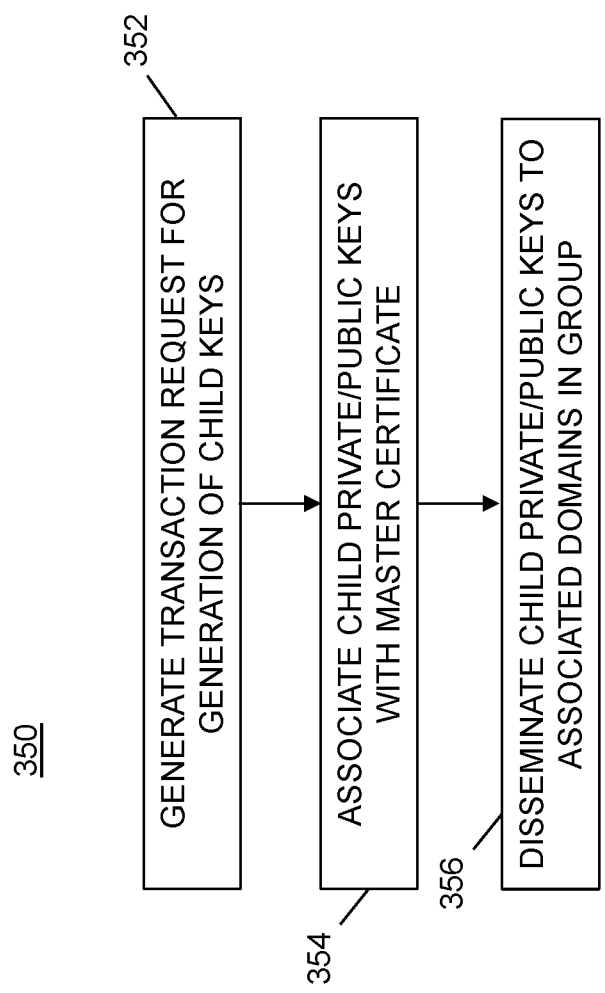
FIG. 4 is flow chart of a method of generating one or more child keys for one or more domains within a group of domains, in accordance with some embodiments.

FIG. 4 illustrates a method 350 for generating one or more child keys for one or more domains within a group of domains. At step 352, a client device 104 generates a transaction request including a request for the registration of one or more child key pairs. In some embodiments, the transaction request is generated using one or more device-related identifiers, a proposed child public/private key, and/or any other suitable information. In other embodiments, the CA 150 automatically generates one or more child key pairs after registering a master key pair for a domain/group. In some embodiments, the child public/private key is derived from the master public/private key using one or more key derivation functions (KDF) such as a keyed cryptographic hash function, although it will be appreciated that any suitable KDF can be used. The child public/private key can be derived by the client device 102 prior to generation of the transaction request, derived by the CA 150 during processing of the transaction request, and/or generated by a key generator stored on a remote system.

At step 354, the CA 150 associates the one or more derived child private/public keys with the master public/private key and/or the master certificate. For example, in some embodiments, the CA 150 updates the master certificate to include the one or more child public/private keys. In another embodiment, the CA 150 updates an accumulator configured to identify valid keys to include the one or more child public/private keys.

At step 356 the one or more child public/private keys are provided to one or more of the domains within the group associated with the master key. The child keys are configured for use in transmission and/or receipt of messages to and/or from the identified domain. For example, as discussed in more detail below, one or more child public/private keys can be used to generate one or more session keys for path agnostic transmission over a distributed nodal network. In other embodiments, the one or more child public/private keys can be used to sign transactions uploaded to the CA 150 and/or the distributed ledger 200. In some embodiments, the child public/private keys are used by one or more client devices 102 to generate encrypted messages for path agnostic transmission over a distributed nodal network.

Figure 5:
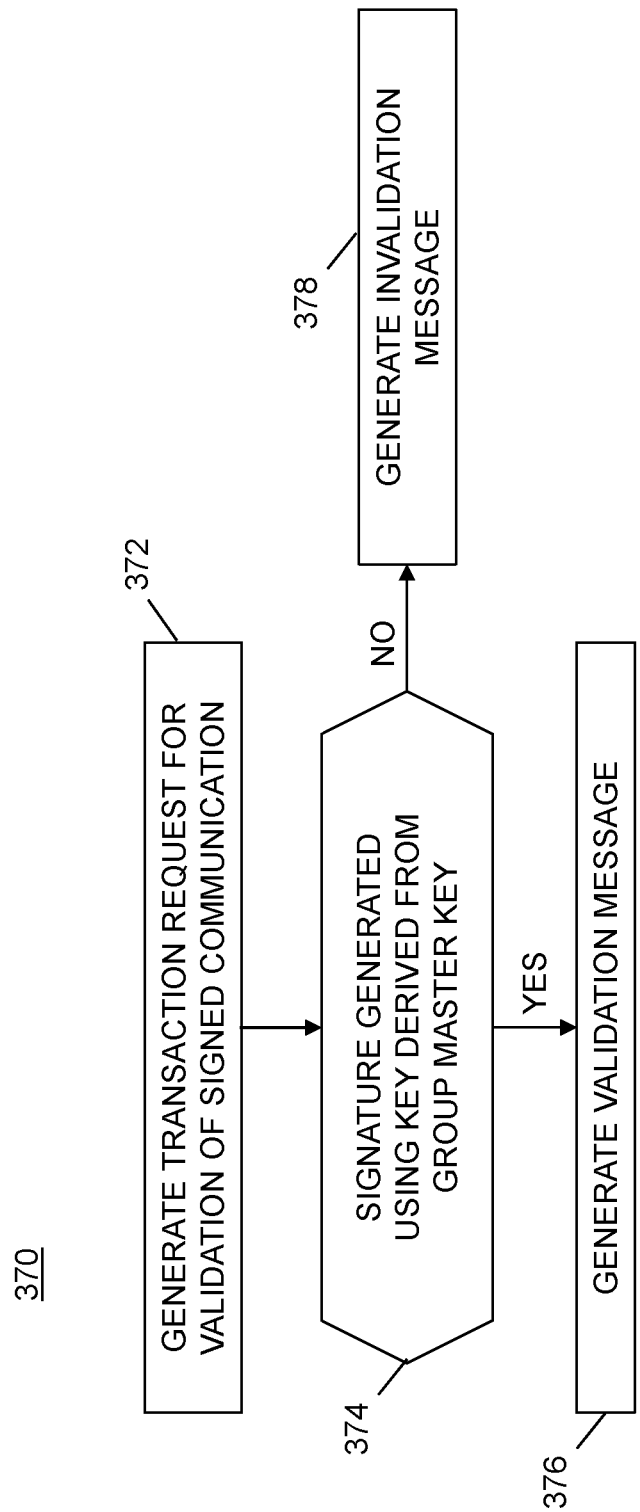
FIG. 5 is a flow chart illustrating one embodiment of a method of validating a child public/private key, in accordance with some embodiments.

FIG. 5 is a flow chart illustrating one embodiment of a method 370 of validating a child public/private key. At step 372, a device, such as an intermediate device 106, 108, generates a transaction request to the CA 150 requesting validation of a signature on one or more communications received by the device. For example, in some embodiments, the communication includes one or more messages received by the intermediate device 106, 108 and intended for forwarding to additional devices. The validation request includes the signature provided with the communication.

At step 374, the CA 150 determines whether the signature was generated using a public/private key derived from a master key associated with a group including a source domain of the message. For example, in some embodiments, the CA 150 utilizes one or more verification techniques, such as a verification technique associated with the KDF used to generate one or more child private/public keys. In some embodiments, the signature is verified using one or more accumulators configured to maintain a current state of multiple public/private keys registered with the CA 150.

If the signature is validated, the CA 150 generates a validation message at step 376. The validation message indicates that the public/private key used to sign the communication is derived from a master public/private key associated with a group and registered on the CA 150. The validation message only indicates that the public/private key used to sign the communication was derived from the master public/private key but does not identify the specific child key and/or domain associated with the specific child key used to sign the communication.

If the signature is not validated, the CA 150 generates an invalid message at step 378. The invalid message indicates that the public/private key used to sign the communication is not derived from a master public/private key associated with the group and registered on the CA 150. Child public/private keys can be used to provide path agnostic secure transmission over a distributed network.

Exemplary Certificate Authority for Obfuscation

In some embodiments, the CA 150 can be configured to provide one or more group certificates configured to ensure trust in a received communication while hiding the individual member of a group that generated the communication. For example, in some embodiments, one or more domains (or client devices 102, 104) can obtain membership in a first group. The first group can be any suitable group, such as, for example, an industry group (such as a group of brokers, financial institutions, etc.), a group of domains owned by a single entity, a group of domains of related services, a group of client devices 102, 104 in a private network, and/or any other group ID of devices (and/or associated domains/identifiers.

Figure 6:
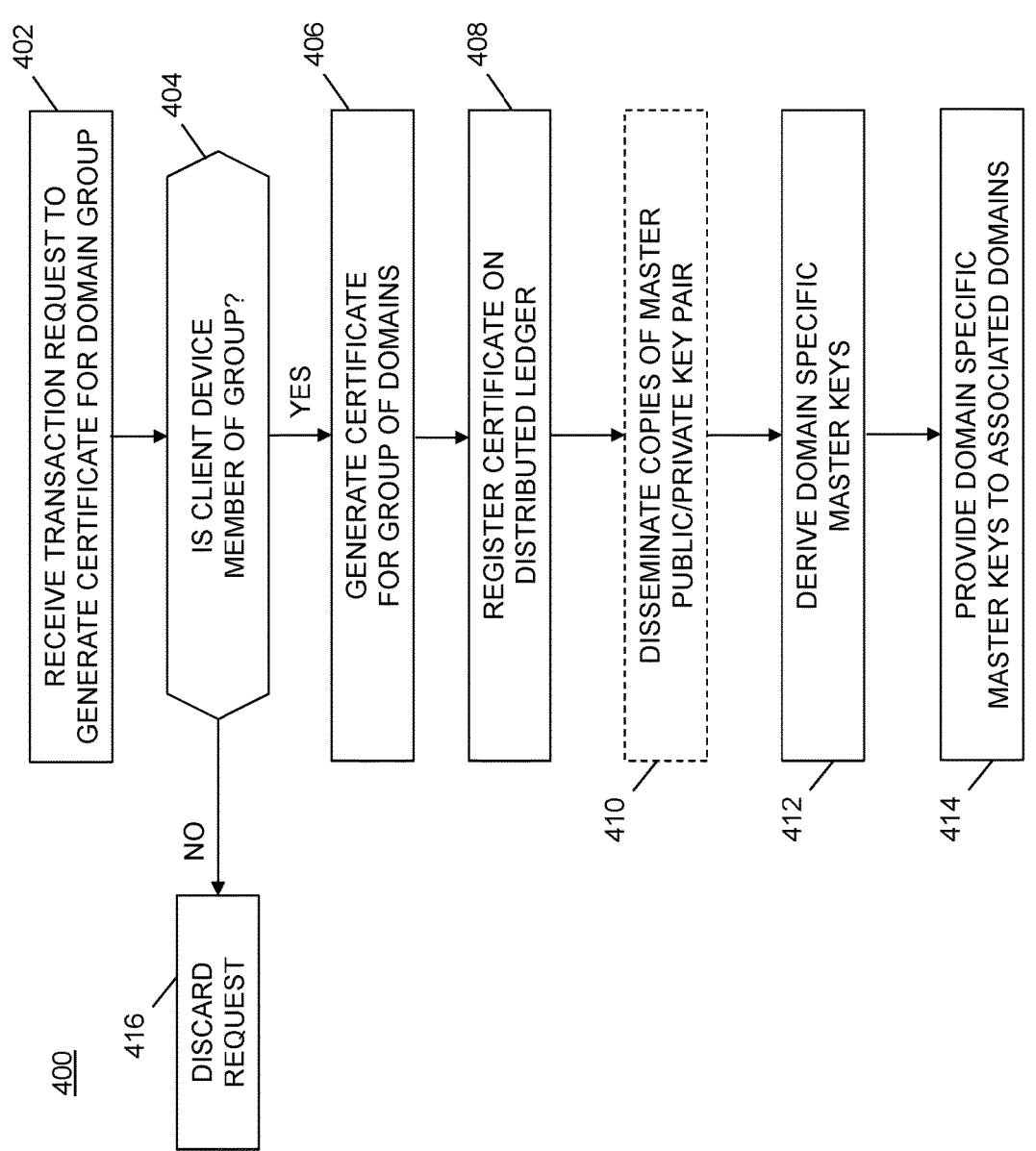
FIG. 6 is a flow chart illustrating one embodiment of a method for generating a master key and deriving one or more domain specific keys, in accordance with some embodiments.

FIG. 6 illustrates one embodiment of a method 400 for generating a master key and deriving one or more domain specific keys, in accordance with some embodiments. At step 402, the CA 150 receives a transaction request from one or more domains associated with a group. For example, in some embodiments, a member of the first group, such as a first client device 102, generates a certificate registration transaction request in accordance with the method 300 discussed above. The registration transaction request can include a proposed group master public/private key pair generated by the first client device 102, for example, using a key generator stored on and/or separately from the client device 102.

At step 404, the CA 150 verifies the first client devices membership in the first group. In some embodiments, the CA 150 verifies the first client device 102 by generating a web call to a domain associated with the first client device. The web call includes a secure group code. The domain associated with the first client device responses with a valid shared token indicating membership in the group. In some embodiments, validation of a single client device 102 in the group is enough to validate the first group as a whole. If the domain associated with the first client 102 is verified, the method proceeds to step 406. Otherwise, the method exits and the registration request is discarded at step 416.

At step 406, the CA 150 issues a master certificate associated with a first group of domains and/or client devices. In some embodiments, the CA 150 can generate the group master public/private key pair when generating the master certificate, for example, using a predetermined key generator. In some embodiments, the CA 150 generates the master public/private key pair using one or more known key generation algorithms. The CA 150 can use a random number seed, for example, a noise signal received from one or more domains in the group.

At step 408, the CA 150 registers a certificate in accordance with the method 300 and associates the certificate with the first group. For example, in some embodiments, the CA 150 generates a certificate associated with each of the domains and/or client devices.

At optional step 410, the CA 150 and/or the first client device 102 disseminates copies of the master public/private key to each of the domains in the first group. For example, in some embodiments, the CA 150 sends a secure message to each of the domains including copies of the group master public/private keys. In other embodiments, the first client device 102 (or the associated first user 110) disseminates copies of the master public/private keys using one or more offline distribution channels, such as mail. In other embodiments, the group master public/private keys are not disseminated and can be stored on the distributed ledger 200.

At step 412, one or more domain-specific master keys are derived from the group master public/private keys. The one or more domain-specific master keys can be derived using any suitable key derivation function (KDF), such as a keyed cryptographic hash function. The one or more domain-specific master keys can be derived by the CA 150 and/or by one or more client devices 102, 104. In some embodiments, the master certificate is updated to include the one or more derived domain-specific keys. For example, in some embodiments, the certificate includes one or more data fields configured to store domain-specific master public keys.

In some embodiments, a random number seed is provided for derivation of each of the domain-specific master keys. For example, in some embodiments, a noise signal provided from each of the domains in the first group is used as a random number seed for a KDF to derive one of the domain-specific public/private key pairs. In other embodiments, the noise signals can be combined to generate one or more random number seeds.

At step 414, at least one of the one or more domain-specific master keys is distributed to each of the domains in the first group. For example, in some embodiments, a first domain-specific public/private key pair is derived from the master private key for each of the domains in the group and distributed to the respective domain. In other embodiments, each of the domains in the group generate individual domain specific master keys derived from, for example, a master public key shared with the members of the first group.

In some embodiments, each of the domain-specific master keys configured to expire after a predetermined time. For example, in some embodiments, each of the generated domains-specific master keys has a predetermined expiration period. After the predetermined expiration period, the CA 150 invalidates the domain-specific public/private master key pair. The CA 150 can generate a new public/private key pair for the specified domain automatically and/or can wait for a transaction request from the associated domain.

Figure 7:
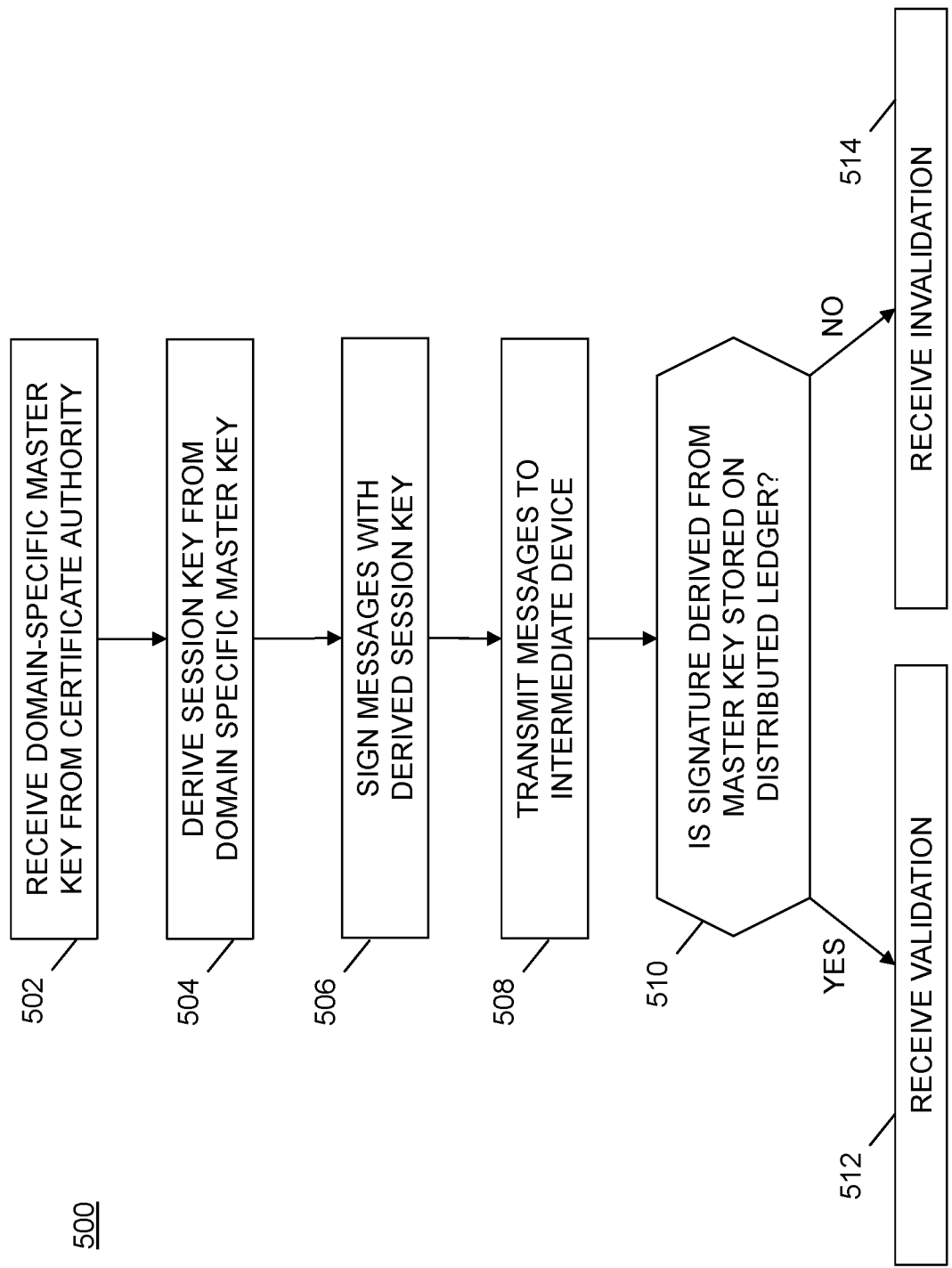
FIG. 7 illustrates a method of validating a signature at the CA, in accordance with some embodiments.

In some embodiments, the individual domains can generate session specific keys derived from a domain-specific master key. FIG. 7 illustrates a method 500 of generating one or more group-signed messages, in accordance with some embodiments. At step 502, a client device 102 receives a domain-specific master key from a CA 150. The domain-specific master key can be generated and/or associated with a certificate issued by the certificate authority, for example, according to any suitable method, such as, the method 400 discussed above.

At step 504, the first client device 102 derives a session key from the domain-specific master key. The session key can be generated according to any suitable KDF, such as a keyed cryptographic hash function. In some embodiments, the KDF used to generate the domain-specific master key can be the same and/or different than the KDF used to generate the session keys.

At step 506, the first client device 102 signs one or more messages using the session key. The client device 102 can sign the one or more messages using any suitable signature protocol, such as, for example, an RSA key signing protocol, a PGP key signing protocol, and/or any other suitable signing protocol.

At step 508, the first client device 102 transmits the one or more messages to one or more additional devices, such as intermediate device 106. The one or more messages can be transmitted over a communications network 120.

At step 510 the intermediate device 106 verifies the signature of the message. For example, in some embodiments, the intermediate device 106 generates a verification request that is transmitted to the CA 150. In some embodiments, the CA 150 verifies the signature according to one or more methods, such as the method 370 described above.

If the signature is valid, at step 512, the intermediate device 106 receives verification from the CA 150. The verification indicates whether the message received at the intermediate device 106 was signed with a key derived from the group master public/private key without revealing which of the domains in the group generated and/or signed the message. The intermediate node 106 can trust that the message is authentic and sent from one of the members of the group and can be trusted.

If the signature is invalid, at step 514, the intermediate device 106 receives an invalidation message from CA 150 and discards the message.

The methods and system described herein may be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. An apparatus, comprising:
a communications unit;
a storage device; and
a processor coupled to the communications unit and to the storage device, the storage device storing software instructions for controlling the processor that when executed by the processor configured the processor to:
generate a master key generation request, the master key registration request comprising a random number seed and data that identifies a group including one or more domains, and wherein the apparatus is associated with at least one of the one or more domains;
transmit, via the communications unit, the master key generation request to a computing system, the computing system maintaining a copy of a distributed ledger, the distributed ledger having a ledger block that includes additional instructions associated with a certificate authority, and the computing system being configured to execute the additional instructions to generate a master public and private key pair;
receive, via the communications unit, a secure group code associated with the group from the computing system;
in response to the receipt of the secure group code, transmit, via the communications unit, a shared token associated with the at least one domain to the computing system, the computing system being configured to execute the additional instructions to: verify a membership of the at least one domain within the group based on the shared token; based on the verified membership, generate a certificate associated with the master public and private key pair and further associate the generated certificate with data that identifies the group and the plurality of domains; and perform operations that record the generated certificate and the associated data within an additional ledger block of the distributed ledger, the recordation of the generated certificate and the associated data registering the certificate to the group; and
receive, via the communications unit, and from the computing system, a domain-specific key derived from the master public and private key pair.

2. The apparatus of claim 1, wherein the processor is further configured to:
derive a session key from the domain-specific key; and
apply a digital signature to message data using the session key.

3. The apparatus of claim 1, wherein the random number seed includes a noise signal generated by one of the plurality of domains.

4. The apparatus of claim 1, wherein:
the processor is further configured to receive a secure group call that includes the secure group code; and
the shared token corresponds to a group token identifying the apparatus as being associated with the at least one of the plurality of domains.

5. A computer-implemented method, comprising:
generating a certificate generation request using at least one processor, the certificate generation request comprising data characterizing a plurality of domains associated with a group;
transmitting, using the at least one processor, the certificate generation request to a computing system, the computing system maintaining a copy of a distributed ledger, the distributed ledger having a ledger block that includes instructions associated with a certificate authority; and
receiving, using the at least one processor, a secure group code associated with the group from the computing system;
in response to the receipt of the secure group code, transmitting, using the at least one processor, and to the computing system, a shared token associated with at least one of the plurality of domains, the computing system being configured to execute the instructions to: verify a membership of the at least one domain within the group based on the shared token; based on the verified membership, to generate a certificate associated with the master private and public key pair and further associate the generated certificate with data that identifies the group and the plurality of domains; and perform operations that record the generated certificate and the associated data within an additional ledger block of the distributed ledger, the recordation of the generated certificate and the associated data registering the certificate to the group; and
receiving, using the at least one processor, at least one derived domain-specific key from the computing system, the derived domain-specific key being derived by the computing system from a master group key associated with the group.

6. The method of claim 5, wherein the certificate generation request includes a random number seed generated from one or more noise signals of the plurality of domains.

7. The method of claim 5, wherein:
receiving the shared group code comprises receiving a network-based call associated with the certificate authority, the network-based call including at least one identity challenge; and the transmission of the shared token corresponds to a response to the at least one identity challenge; and the shared token corresponds to a predetermined token associated with the at least one identity challenge.

8. The method of claim 5, further comprising:

deriving a session specific key from the derived domain-specific key; and applying a digital signature to message data using the session specific key.

9. The method of claim 5, further comprising receiving, from the computing system, a first derived domain-specific key and a second derived domain-specific key, wherein the second derived domain-specific key is received a predetermined time period after the first derived domain-specific key, and wherein the second derived domain-specific key invalidates the first derived domain-specific key.

* * * * *